United States Patent [19]
McRoberts et al.

[11] Patent Number: 5,807,299
[45] Date of Patent: *Sep. 15, 1998

[54] MALE GENITALIA SUPPORTER

[75] Inventors: Samuel J McRoberts, Palm Beach Gardens; Lee Kvarnberg, Jupiter, both of Fla.

[73] Assignee: Male Pouch, Inc.

[ * ] Notice: The term of this patent shall not extend beyond the expiration date of Pat. No. 5,547,466.

[21] Appl. No.: 699,595

[22] Filed: Aug. 19, 1996

Related U.S. Application Data

[63] Continuation-in-part of Ser. No. 419,467, Apr. 10, 1995, Pat. No. 5,547,466.

[51] Int. Cl.⁶ ..................................................... A61F 13/00
[52] U.S. Cl. ............................................... 602/67; 602/70
[58] Field of Search .................................. 602/67, 70, 72, 602/73

[56] References Cited

U.S. PATENT DOCUMENTS

| | | |
|---|---|---|
| 64,766 | 5/1867 | Heaton ...................................... 602/70 |
| 77,757 | 5/1868 | Phelps . |
| 214,888 | 4/1879 | Cooper et al. ............................. 602/73 |
| D. 233,633 | 11/1974 | Burkard . |
| 265,672 | 10/1882 | Hart . |
| 286,657 | 10/1883 | Ware . |
| 531,232 | 12/1894 | Teuscher, Jr. . |
| 713,318 | 11/1902 | Lovis . |
| 850,298 | 4/1907 | De Mars . |
| 908,533 | 1/1909 | Zuckriegel . |
| 967,736 | 8/1910 | Delp . |
| 1,019,501 | 3/1912 | Love et al. . |
| 1,023,478 | 4/1912 | O'Reilly . |
| 1,350,863 | 8/1920 | Fowler . |
| 1,477,187 | 12/1923 | Rayne . |
| 1,483,351 | 2/1924 | Keirstead . |
| 1,638,525 | 8/1927 | Chisholm . |
| 1,742,399 | 1/1930 | Klein . |
| 2,293,998 | 8/1942 | Norwood . |
| 2,320,736 | 6/1943 | Nevins . |
| 2,427,428 | 9/1947 | Vitale . |
| 2,686,517 | 8/1954 | Boyd . |
| 2,746,456 | 5/1956 | Johnson . |
| 2,798,484 | 7/1957 | Boudreaux . |
| 2,888,014 | 5/1959 | Dougherty . |
| 3,225,761 | 12/1965 | Swensen . |
| 3,314,422 | 4/1967 | Phillips . |
| 3,518,995 | 7/1970 | Claff . |
| 3,550,590 | 12/1970 | Keilman . |
| 4,122,849 | 10/1978 | Dietz . |
| 4,141,357 | 2/1979 | Dietz . |
| 4,195,630 | 4/1980 | Connery et al. . |
| 4,505,707 | 3/1985 | Feeney . |
| 4,576,599 | 3/1986 | Lipner . |
| 4,627,846 | 12/1986 | Ternström . |
| 4,660,554 | 4/1987 | Wright . |
| 4,731,063 | 3/1988 | Newkirk . |
| 5,029,345 | 7/1991 | Angheluta et al. . |
| 5,157,793 | 10/1992 | Michels . |
| 5,275,592 | 1/1994 | Grizzaffi . |
| 5,401,266 | 3/1995 | Runeman et al. . |
| 5,547,466 | 8/1996 | McRoberts et al. . |

*Primary Examiner*—Robert A. Clarke
*Attorney, Agent, or Firm*—Thomas E. Coverstone

[57] ABSTRACT

A male genitalia supporter has a posterior testicular strap portion extending from a waist band portion. The posterior testicular strap portion is designed to be positioned behind the scrotum and the testicles to provide support to the wearer's scrotal contents. The support is made of a generally unyielding material so that a constant, non-variable amount of support is provided to the wearer. A receptacle, made of an air-permeable and absorbent material, for accepting the male's genitalia is attached to the supporter.

43 Claims, 9 Drawing Sheets

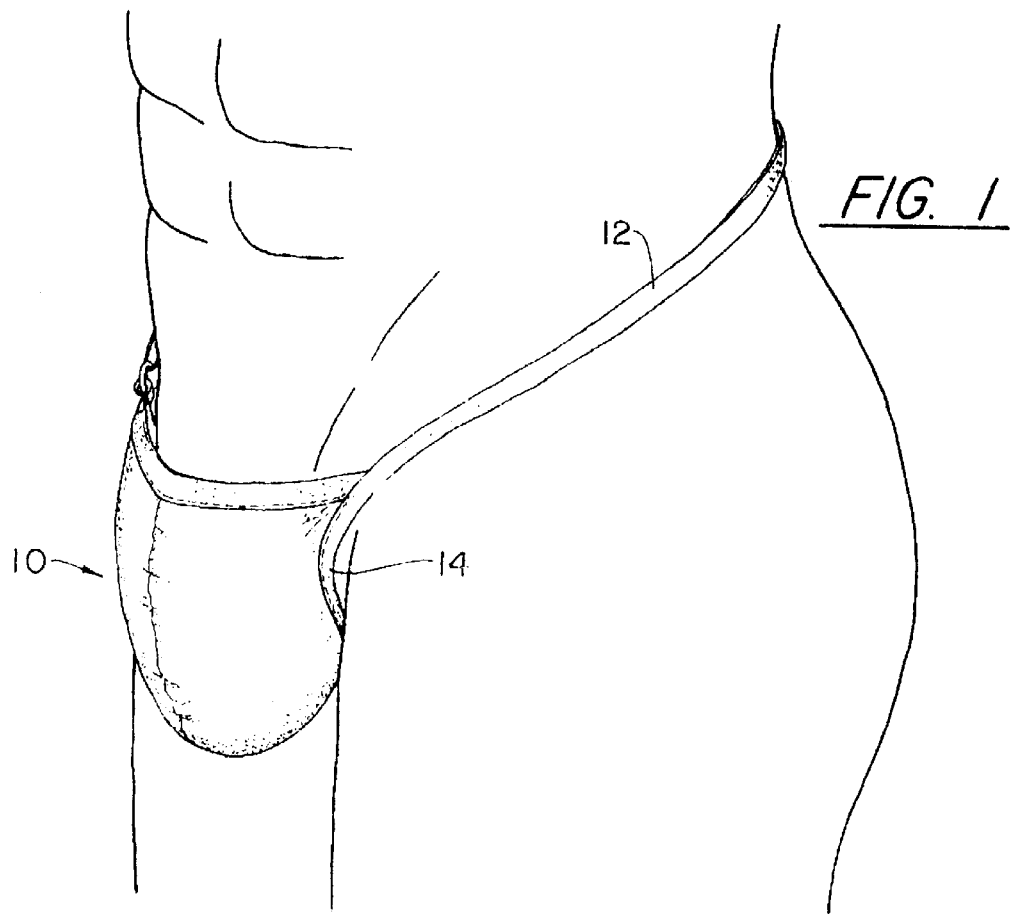
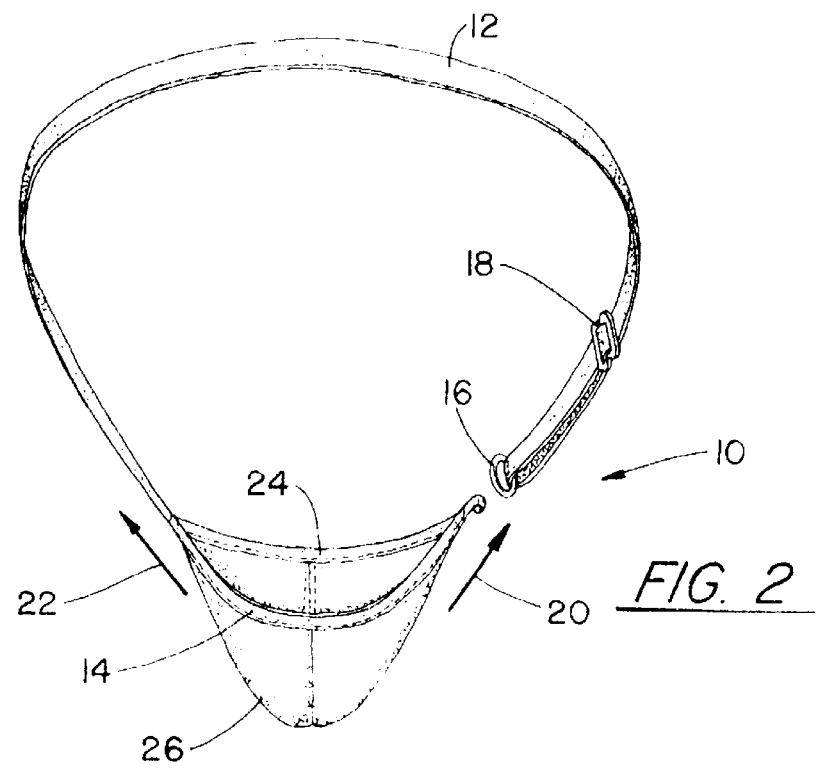

MALE GENITALIA SUPPORTER

This application is a continuation in part of Ser. No. 08/419,467 filed Apr. 10, 1995 now U.S. Pat. No. 5,547,466.

TECHNICAL FIELD OF THE INVENTION

This invention relates to support devices for male genitalia, and more particularly, to a male genitalia supporter useful particularly after surgery, wherein the device provides a generally constant amount of support to the male genitalia.

BACKGROUND OF THE INVENTION

Support garments for male genitalia are well known. The waist band or an elastic waist band in combination with leg or crotch straps.

Absorbent support garments typically include a variation of the known support garments with the attachment of an absorbent receptacle to accommodate the penis to absorb drainage from the penis. Other absorbent support garments may include an absorbent sack to accommodate the scrotum and to absorb drainage from the scrotum area or from a drainage tube, such as after surgery.

For example, U.S. Pat. No. 2,888,014 issued to Dougherty discloses a suspensory that has a receptacle that is supported by three straps. Two straps encircle the legs and the third strap encircles the waist. An absorbent pad is used with the suspensory when the wearer has urinary infections.

U.S. Pat. No. 3,550,590 issued to Keilman discloses a bandage with a receptacle for the penis, the receptacle is supported by a waist strap.

U.S. Pat. No. 4,195,630 issued to Connery et al. discloses an undergarment with a penis opening and a complimentary flap receptacle for accepting the end of the penis.

U.S. Pat. No. 4,576,599 issued to Lipner discloses a disposable sanitary pad for men, the pad is unfolded and placed around the penis. Adhesive or hook and loop fasteners attach the pad to the wearer's clothes.

The absorbent male supporters available to date attempt to provide support with absorbent components; however, it is evident when reviewing the past supporters that the designs are insufficient in the amount of continuous and non-variable support given to the male genitalia while trying to provide an absorbent feature. More particularly, the supporters of the past do not address the need for having an absorbent supporter for males who have undergone a surgical procedure with drainage occurring at the scrotum or the penis, while providing support of the scrotum and the testicles to prevent excessive strain upon the cremaster muscles and the spermatic cords.

Such a support of the scrotum and testicles is desired after minor surgery, such as a vasectomy, or during and after a case of epididymitis, where support of the cremaster muscles and the spermatic cords, or the scrotal contents, aids in the patient's healing process and raises the patient's comfort level during these events.

In addition, the supporters of the past do not address maximum absorbency while allowing the passage of air for the ventilation of the wearer's genital area. Without ventilation, the wearer would become hot and perspiration would occur. The wearer would become uncomfortable and would be prone to the growth of fungi and bacterial infections at the genital region. The growth of fungi and bacteria in the genital area should be avoided, especially after surgery in the genital area. A surgical incision after surgery should have an adequate and proper amount of ventilation of fresh air to promote healing.

Most of the available supporters are designed to be made of a yielding material so that the supporter flexes with the movements of the wearer. For example, Dietz (U.S. Pat. No. 4,122,849) discloses the use of an elastic strap at the top edge of the pouch so that the cup's shape and cubic volume fluctuates as the wearer moves about and the elastic is stretched. Therefore, as the wearer of the supporter would move about in his daily activities, and as the wearer's lower torso moves, the cup's shape would be constantly fluctuating in shape and cubic volume, which would result in a varying amount of support given to the wearer's scrotum and testicles. The basic design of the currently available supporters would certainly be uncomfortable for the wearer after surgery or after an illness; it would also be uncomfortable to an every day user absent the surgery or illness.

Therefore, what is needed is a male genitalia supporter with that emphasizes support at the scrotum for the testicles, and more particularly, a supporter for the scrotal contents and cords.

DISCLOSURE OF THE INVENTION

It is, therefore, an object of the present invention to provide an absorbent male genitalia supporter that provides generally a constant and non-variable, but adjustable, amount of support to the testicular muscles and cords.

It is also an object of the present invention to provide a male genitalia supporter that has absorbent components to absorb discharge fluids from the male genitalia.

It is also an object of the present invention to provide a male genitalia supporter that allows for thermal conditioning of the male genitalia.

It is also an object of the present invention to provide an absorbent male genitalia supporter that is disposable, lightweight, and comfortable to wear.

It is also an object of the present invention to provide an absorbent male genitalia supporter that provides for the ventilation of air at the genitalia region while being worn.

It is also an object of the present invention to provide an absorbent male genitalia supporter that supports the scrotum and testicles to prevent excessive strain upon the cremaster muscles and the spermatic cords, or generally, the scrotal contents.

It is also an object of present invention to provide an absorbent male genitalia supporter that may be used after surgery, such as a vasectomy, hydrocelectomy, or during and after an illness, such as a case of epididymitis or orchitis, where the supporter aids in the patient's healing process and raises the patient's comfort level during these events.

It is also an object of the present invention to provide an absorbent male genitalia supporter that provides a constant, non-variable amount of support to the posterior side of the scrotum and testicles, and more particularly, to the scrotal contents.

It is also an object of the present invention to provide a male genitalia supporter that may be incorporated into ordinary clothing, such as boxer shorts, swimsuits, and active wear.

According to the present invention, a male genitalia supporter has a posterior testicular strap portion extending from a waist band portion. The posterior testicular strap portion is designed to be positioned behind the scrotum and testicles. The posterior testicular strap portion is an extension of the waist band portion, so that the waist band portion provides support to the testicular strap portion while the supporter is worn. A lateral strap portion extends laterally from the waist band portion across the anterior side of the lower torso area of the wearer. In the preferred embodiment, an absorbent receptacle for accepting the male's genitalia is attached to the supporter, the receptacle extends from the posterior testicular strap portion to the lateral strap portion. The receptacle accepts and houses the wearer's scrotum, testicles, and penis. The receptacle is made of an absorbent and non-stick material so that the supporter is well suited for use after surgical procedures or medical conditions where drainage occurs from the genitalia.

In combination, the waist band portion and the testicular strap portion establish a line of support for the scrotum and testicles. The waist band portion and the testicular strap portion are made of a material that has a relatively high tensile strength. Therefore, the line of support provides generally a constant, non-variable amount of support to the cremaster muscles and the spermatic cords, or generally, the scrotal contents and the testicular muscles and cords.

The waist band portion has a fastening means for fastening the waist band portion to the posterior testicular strap portion after the waist band portion is positioned around the waist of the wearer. The waist band portion has an adjusting means for adjusting the length of the waist band portion, and ultimately, the amount of support given by the testicular strap portion to the scrotum and the testicles. Therefore, the wearer adjusts the supporter to his own comfort level. The waist band portion may be adjustable to accommodate wearers of a variety of waist sizes.

The supporter is made from a lightweight, air-permeable, but absorbent fabric. The fabric is constructed to create the receptacle for the scrotum, testicles, and penis. The receptacle has a pair of external pockets so that cold packs or heat packs may be placed in the pockets, providing thermal conditioning to the genitalia.

In a separate embodiment, a male genitalia supporter is sewn to ordinary clothing, such as boxers, swimsuits, active wear or the like. The supporter is similar to the above described preferred embodiment, except that the waist band portion is adjustable through the garment waist band. The waist band portion has an elastic portion and fastens at the side so that the posterior testicular strap is adjustable. The waist band elastic portion secures the waist band portion to the garment waist band of the garment even while the waist band portion of the supporter is not fastened. Therefore, the garment is placed on the wearer with the waist band portion not fastened, and the elastic band portion allows the waist band portion to stretch while the garment is placed over the wearer's buttocks. Then the waist band portion is adjusted and fastened to provide the proper amount of support.

In combination, the waist band portion and the testicular strap portion establish a line of support for the scrotum and testicles. The waist band portion and the testicular strap portion are made of a material that has a relatively high tensile strength. Therefore, the line of support provides generally a constant, non-variable amount of support to the testicular muscles and cords, even while the wearer is wearing a non-supporting garment, such as boxer shorts.

The foregoing and other advantages of the present invention will become more apparent from the following description and accompanying drawings.

BRIEF DESCRIPTION OF THE DRAWINGS

FIG. 1 is a front perspective view of an absorbent male genitalia supporter of the present invention, as worn by the wearer.

FIG. 2 is a aft perspective view of the absorbent male genitalia supporter of the present invention.

Figure 3:
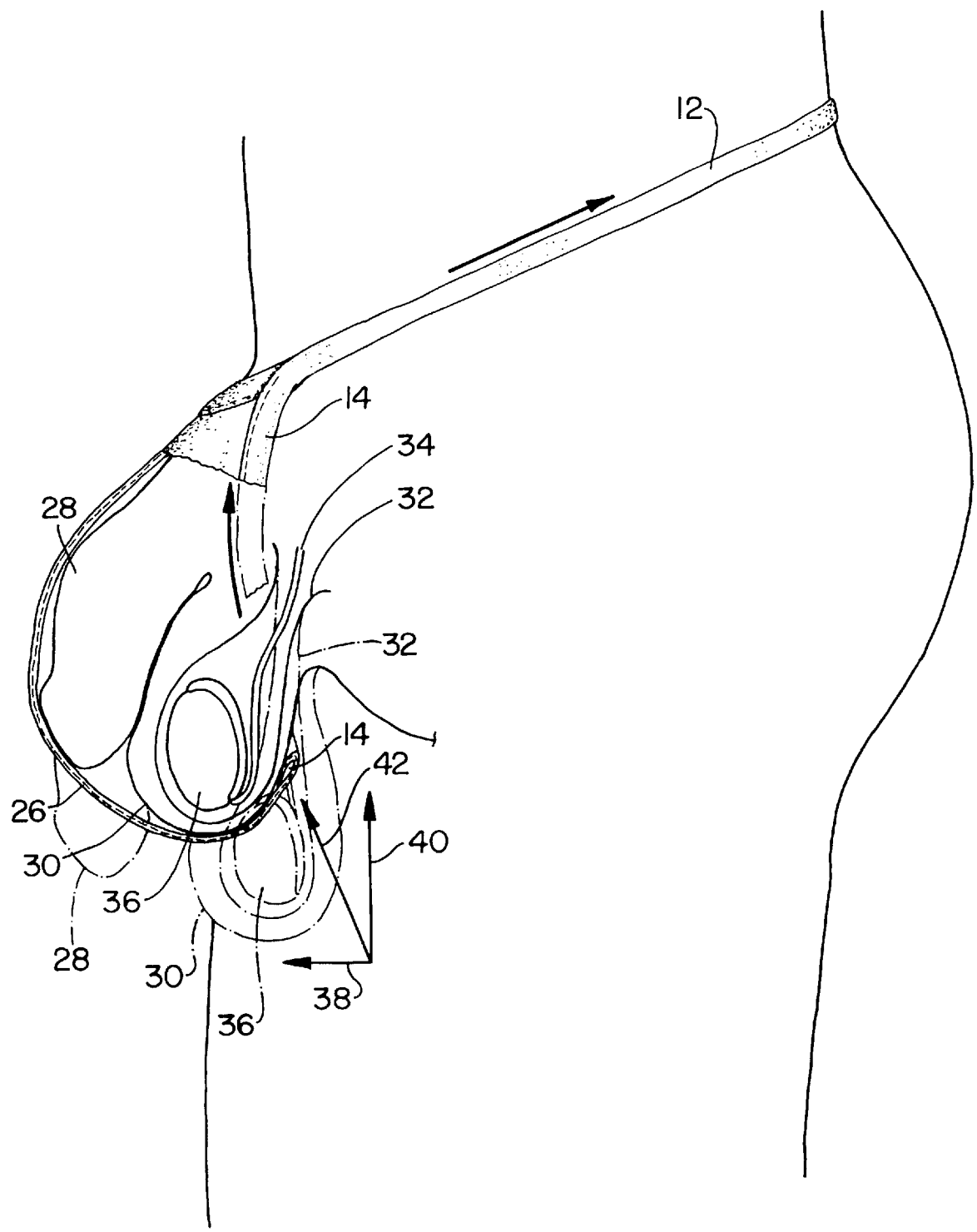
FIG. 3 is cross sectional view of the absorbent male genitalia supporter of the present invention showing the area of support given to the male genitalia of the wearer.

BEST MODE FOR CARRYING OUT THE INVENTION:

According to the present invention, and as shown in FIG. 1, an absorbent male genitalia supporter 10 is provided to give support to the wearer's scrotum and testicles.

The scrotum is a pouch of skin lying below the pubic symphysis and in front of the upper parts of the thighs. The scrotum contains the testes, or both testicles, and the lowest parts of the spermatic cords.

Below the skin of the scrotum is a layer of involuntary muscle, the dartos, which alters the appearance of the scrotum. The cremaster muscle is a thin muscle layer covering the spermatic cord through which sperm travels. The function of the cremaster muscles is to pull the testicles toward the body in response to cold temperature or stimulation to the nerves.

Beneath the dartos muscle are layers of fascia continuous with those forming the coverings of each of the two spermatic cords, which suspend the testes within the scrotum and contain each ductus deferens, the testicular blood and lymph vessels, the artery to the cremaster muscles, the artery to each ductus deferens, the genital branch of the genito-femoral nerve, and the testicular network of nerves. Therefore, each cord is made up of arteries, veins, lymphatics, nerves, and the excretory duct of the testicles. The spermatic cord is the structure by which each testicle is attached to the body. The left spermatic cord is usually longer than the right, thus the left testis usually hangs lower than the right.

The testes each have an epididymis, which is a long tightly coiled tube that ends in a single tube called the vas deferens, which empties into an ejaculatory duct in the posterior urethra, which carries sperm from the testicle to the tip of the penis. Epididymitis is an inflammation of the epididymis. Epididymitis may result from urinary infection, venereal disease, prostate surgery or trauma.

In regards to the present invention, the scrotal contents, cremaster muscles and spermatic cords, and more generally, the muscles, cords, and ducts that attach and connect the testicles to the pelvis area and the body in general, are referred to in a general sense as testicular muscles and cords.

As shown in FIG. 1, the absorbent male genitalia supporter 10 has a waist band portion 12 that is placed around the waist of the male wearer. Referring now to FIG. 2, the male genitalia support 10 also has a posterior testicular strap portion 14 extending from the waist band portion 12. A fastening means 16 connects the waist band portion 12 to the posterior testicular strap portion 14 for the ease of wearer. Without limiting the scope of the present invention, the preferred embodiment shows a single hook and loop faster 16. Alternative fastening means are discussed below.

In one embodiment, and as shown in FIG. 2, the waist band portion 12 includes an adjustment means 18 so that the waist band portion 12 may be adjusted to accommodate a variety of waist sizes, or to accommodate for the waist line dimensional changes of one particular wearer. The adjustment means 18 also adjusts the amount of support and lift given to the testicles provided by the posterior testicular strap portion 14. The amount of support and lift provided to the testicles may be adjusted according to the wearer's needs and comfort level. The adjustment means 18 is a conventional slide well known in the art, where one end of the waist band portion 12 is fixedly attached to the adjustment means 18 so that the overall length of the waist band portion 12 may be shortened or lengthened by sliding the adjustment means in relation to the waist band portion itself.

When the posterior testicular strap portion 14 is placed on the posterior side of the scrotum and the testicles, and when the waist band portion 12 is placed around the waist of the wearer, support or lift is provided along the posterior testicular strap 14, as generally shown by arrows 20 and 22.

The male genitalia support 10 includes a lateral strap portion 24, connecting to the posterior testicular strap 14. When placed on the wearer, the lateral strap portion 24 extends across the anterior lower torso area of the wearer. Minimal load, if any, is experienced at the lateral strap portion 24. The functional purpose for the lateral strap portion 24 is so that an absorbent receptacle 26 may be attached to the posterior testicular strap 14 and to the lateral strap portion 24. The receptacle 26 accepts and houses the wearer's scrotum, testicles, and penis. The receptacle 26 provides only minor and secondary support to the testicles; the primary lifting and support of the testicles is provided by the posterior testicular strap 14. The receptacle 26, however, does house the absorbent feature of the supporter 10. The receptacle and the absorbent material will be explained in detail below.

Referring now to FIG. 3, the male genitalia support 10 is shown in a cross sectional view as worn by the wearer. The wearer's penis 28 is shown housed in the receptacle 26, as is the wearer's scrotum 30 and testis 36. The cremaster muscle 32 is shown surrounding the spermatic cord 34; the cremaster muscle 32 supports the testes 36. The posterior testicular strap portion 14 is shown on the posterior side of the scrotum 30 and testis 36.

As the posterior testicular strap portion 14 is lifted by the waist band portion 12, a horizontal force vector 38 and a larger vertical force vector 40 combine to give the resultant force vector 42. The resultant force vector, or line of support 42 lifts and supports the testicular muscles and cords of the wearer, relieving the testicular muscles and cords from tensile forces and strain.

The waist band portion 12 and posterior testicular strap 14 are made of generally a non-elastic material that generally does not yield, or yields only a relatively small amount, when placed under tensile stress. The non-elastic material provides support to the testicular muscles and cords that is essentially constant and non-variable. As the wearer walks, sits, or stands, the support given to the testicular muscles and cords is essentially non-variable. This non-variable amount of support, the absorbent features, together with the comfort given to the wearer, combine to be key advantages of the male genitalia support 10 of the present invention over the prior supporters.

The use of the term non-variable support is not to be confused with adjustable support. The male genitalia support 10 has an adjustment means 18 to adjust the amount of support given to the testicular muscles and cords, and once the amount of support is adjusted to the wearer's comfort level, the amount of support is non-variable as the wearer walks, sits, stands, etcetera.

The male genitalia support 10 is particularly useful after surgery to the male genitalia area, such as a vasectomy or hydrocelectomy, or after an illness such as epididymitis or orchitis, or after an injury to the male genital area. Support of the testicular muscles and cords aids in the patient's healing process and raises the patient's comfort level during these events.

To maintain cleanliness at the genitalia site and to provide ease of use, the supporter 10 of the present invention is intended to be disposable. Therefore, a new supporter 10 may be applied in intervals that accommodate the situation. For example, after surgery, the supporter 10 may be replaced every hour, depending on the amount of drainage or leakage at the surgical incision. As drainage from the incision slows or stops, the supporter 10 may be replaced periodically until the incision has healed fully. The design of the supporter of the present invention provides a lifting and separation of the male genitalia from the anal area, which is a high bacteria area. Therefore, the supporter helps in preventing infection at the surgical location by isolating the genitalia.

The use of the male genitalia support 10, however, does not need to be limited to post-surgery, injury, or illness. Some people find the look of boxers and briefs to be unappealing or thongs to be uncomfortable. The male genitalia support 10 provides an alternative undergarment for the male, while providing support and while having an aesthetic appearance. Therefore, the support 10 may be worn as an everyday article of clothing.

As another alternative, the male genitalia supporter 10 may be adapted to be attached or sewn into ordinary undergarments or active wear to the give the supporter 10 a more conventional look and feel. If the supporter is sewn into an existing undergarment or garment, the waist strap and the posterior testicular strap would be independently connected to the garment so that the waist strap and the supporter may be independently adjusted. The male genitalia supporter 10 may also simply be worn underneath ordinary undergarments, such as boxer shorts or briefs, while the wearer benefits from the support given and the absorbent features of the supporter 10.

To reduce the opportunity for bacteria to grow in the male genital area, particularly after surgery in that area, the receptacle 26 is made from an air-permeable and absorbent material that allows the passage of air for the ventilation of the wearer's genitalia area. Ventilation of the area will help to reduce temperature and perspiration. The use of the air-permeable material will increase the wearer's comfort level and reduce the possibility of the growth of fungi. The air-permeable material will help to ventilate the surgical incision after surgery and the ventilation with fresh air will promote healing of the inclusion.

Figure 4:
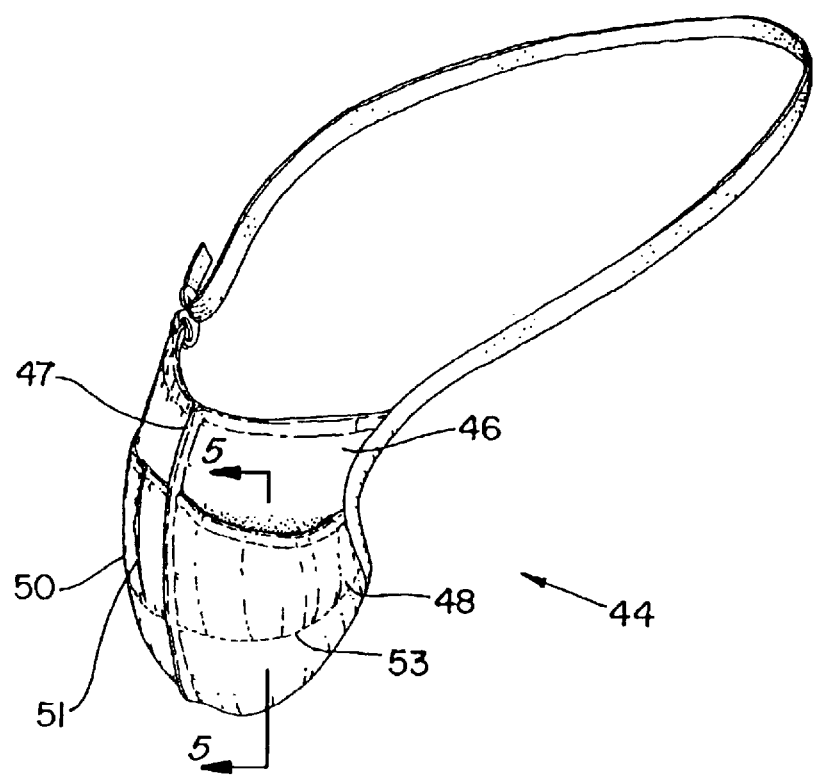
FIG. 4 is a perspective view of an alternative embodiment of an absorbent male genitalia supporter of the present invention with a genitalia thermal conditioning means.
Figure 5:
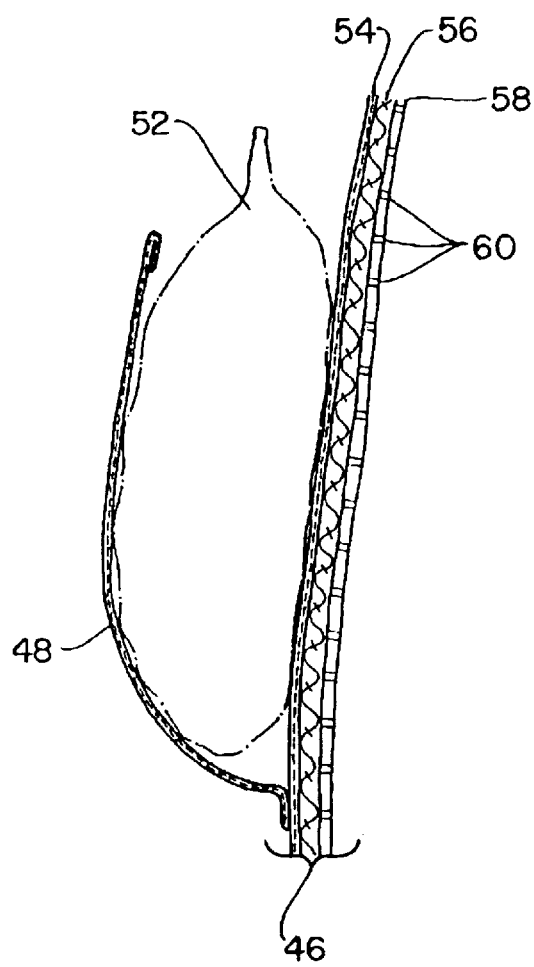
FIG. 5 is a partial cross sectional view taken along line 5—5 of FIG. 4 showing the alternative embodiment absorbent male genitalia supporter.

An alternative embodiment is shown in FIG. 4, where an absorbent male genitalia supporter 44 is shown in perspective view. The supporter 44 is similar to the above described supporter shown in FIG. 1, except supporter 44 has a means for thermally conditioning the genitalia. The supporter 44 has a receptacle 46 with a left pocket 48 and a right pocket 50. The pockets 48 and 50 provide a means for thermal conditioning the male genitalia. The right pocket is shown unextended and the left pocket 48 is shown extended. Each pocket has a pleat, the right pocket 50 is shown with pleat 51. The pleated pockets allow the supporter to have a streamlined appearance until thermal conditioning of the genitalia is desired, then the pockets are extended by unfolding the pleats of material. The pockets 46 and 48 extend forward from the receptacle 46 so that cold packs or heat packs may be placed between the pockets 48 and 50 and the receptacle 46. Typically, cold packs are used after surgery to minimize and reduce inflammation and swelling. The cold packs may take the form of any number of sources, including ice, chilled compresses, or frozen plastic packets containing ammonium nitrate mixed with water. Heat packs are used to relieve the patient from the symptoms of epididymitis and may be used in pockets 48 and 50 when required. As shown in FIG. 5, a cold or heat pack 52 is shown positioned in the left pocket 48.

The recepticle 46 shown in FIG. 4 further has perforations 53 so that the upper portion of the recepticle may be removed so that the recepticle only houses the scrotum and the testicles, leaving the penis uncovered.

The receptacle 46 houses an absorbent material, shown in FIG. 5. The receptacle 46 comprises an outer layer 54, which extends from and is attached to the posterior testicular strap 14. The outer layer 54 and the pockets 48 and 50 are made of an air permeable material similar to the material used in surgical masks or surgical gowns, such as FILTRON TM surgical mask material, which is available from 3M Corp. The panels required to configure the receptacle were successfully bonded together using a combination of heat and pressure applied to the 3M material. As shown in FIG. 4, a seam 47 was created by joining two panels to make the receptacle, the seam 47 extends externally from the receptacle 46 so as not to cause abrasion or irration to the genitalia.

Another prototype was successfully made using a surgical gown material, wherein the two panels for the receptacle were joined by stitching the panels together.

Adjacent to the outer layer 54 is an absorbent layer 56 made up of a plurality of cotton layers. The absorbent layer 54 extends from and is adjacent to the posterior testicular strap 14. The absorbent layer 56 is adjacent to the outer layer 54 and is adapted to be positioned adjacent to the genitalia to capture any discharge from the genitalia or from a genitalia surgical incision. The thickness of the absorbent layer 56 is approximately 0.125 inches, which is sufficient to capture drainage from a leaking incision; however, the thickness of the absorbent layer 56 may be thicker for other applications, such as, if the supporter is being used for incontinent males or if a drainage tube is located in the scrotum.

Adjacent to the absorbent layer 56 is a non-stick layer 58, so that the absorbent layer 56 is sandwiched between the outer layer 54 and the non-stick layer 58. The non-stick layer 58 is a layer of thin, clear plastic with a plurality of relatively small openings 60. The non-stick layer 58 is adapted to be positioned adjacent to the wearer's skin and, in the surgical situation, next to the incision. The plurality of openings 60 allow for the drainage and absorption of fluids from the incision or the drainage tube. The non-stick layer 58 with the openings 60 allow for the absorption of fluids, while providing a non-sticking relationship to the incision when one supporter is to be removed and replaced with a clean supporter. A successful supporter has been made using TELFA TM as the non-stick layer 58. Telfa TM is available from Kendall Co. of Mass.

Figure 11:
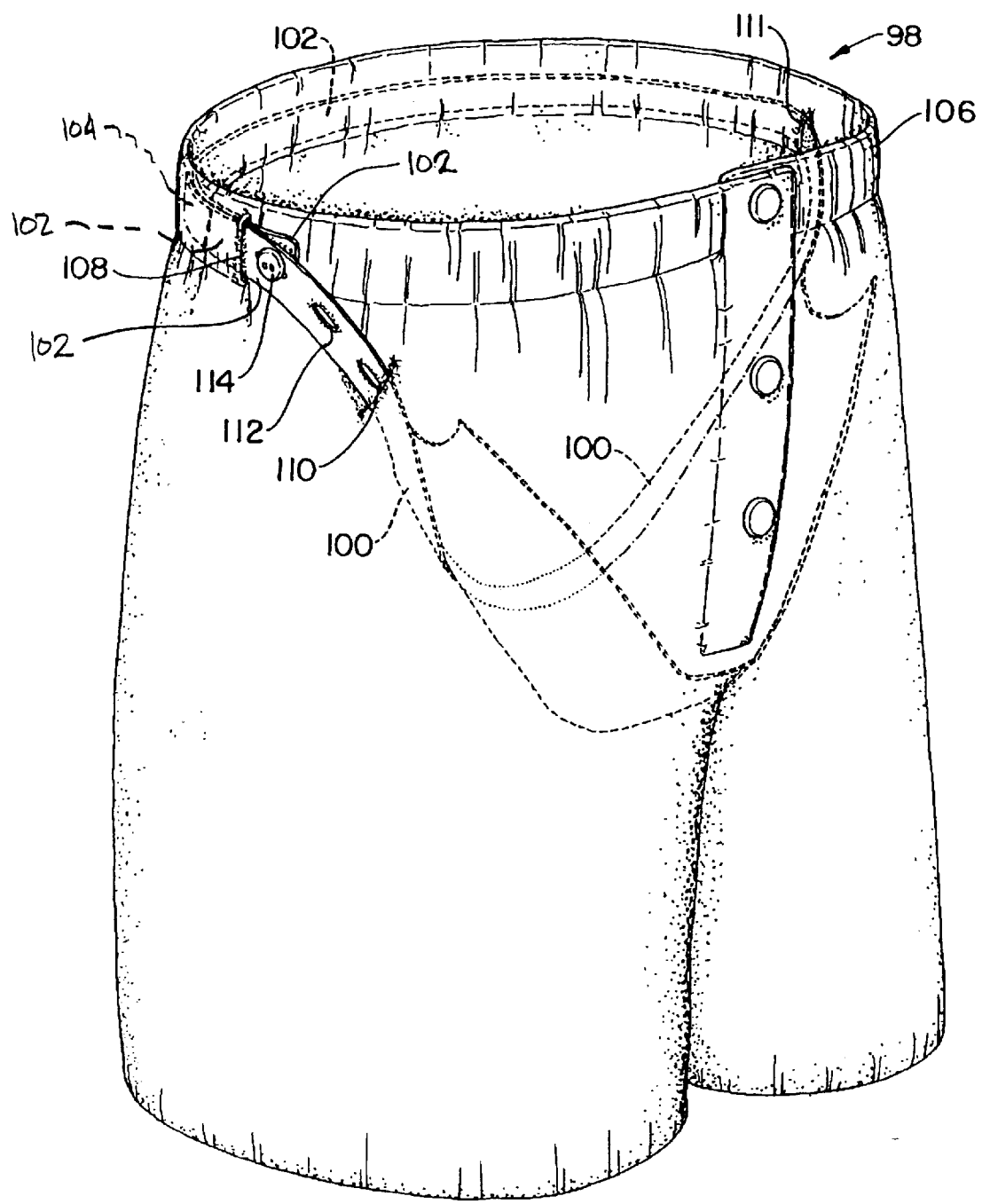
FIG. 11 is a perspective view of yet another embodiment of a supporter of the present invention, where a supporter is incorporated into a garment.

An alternative to the absorbent embodiment shown in FIG. 4 would be an absorbent cup insert that would be inserted into the either of the supporters shown in FIG. 1 or FIG. 11, wherein the insert would be shaped to compliment the receptacle 26.

The fastening means 16 of the present invention may be of a variety of designs, and without limiting the scope of the present invention, two alternative fastening means are described below.

Figure 6:
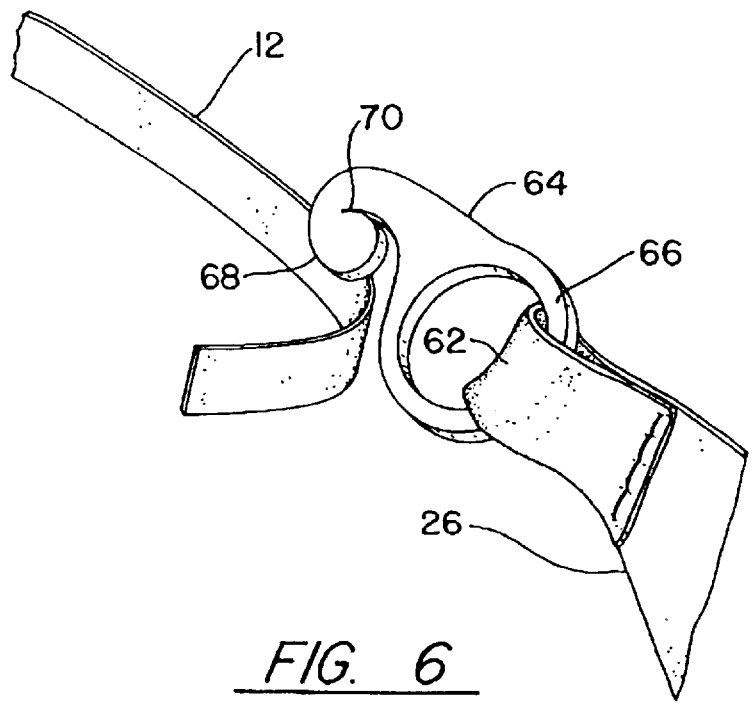
FIG. 6 is a perspective view of an alternative fastening means for the male genitalia supporter of the present invention.

Referring to FIG. 6, a preferred fastening means 64 is shown. The receptacle 26 has a loop 62 of material fastening to the fastening means 64. The fastener 62 has a ring 66 connected to the loop 62, extending from the ring 66 is a hook 68 with an arcuate slot 70. The waist strap 12 is wrapped around the waist of the wearer and placed in the hook 68. The waist strap 12 is adjusted to provide the amount of support desired at the testicles, then the waist strap 12 is slid into the slot 70. The weight of the genitalia drives the waist strap 12 into the slot 70 so that the waist strap 12 is fastened to the fastener 64. If an adjustment of the amount of support is desired, the waist strap 12 is removed from the hook 68 and the slot 70, the support is adjusted, then the waist strap 12 is placed back into the hook 68 and the slot 70.

Figure 7:
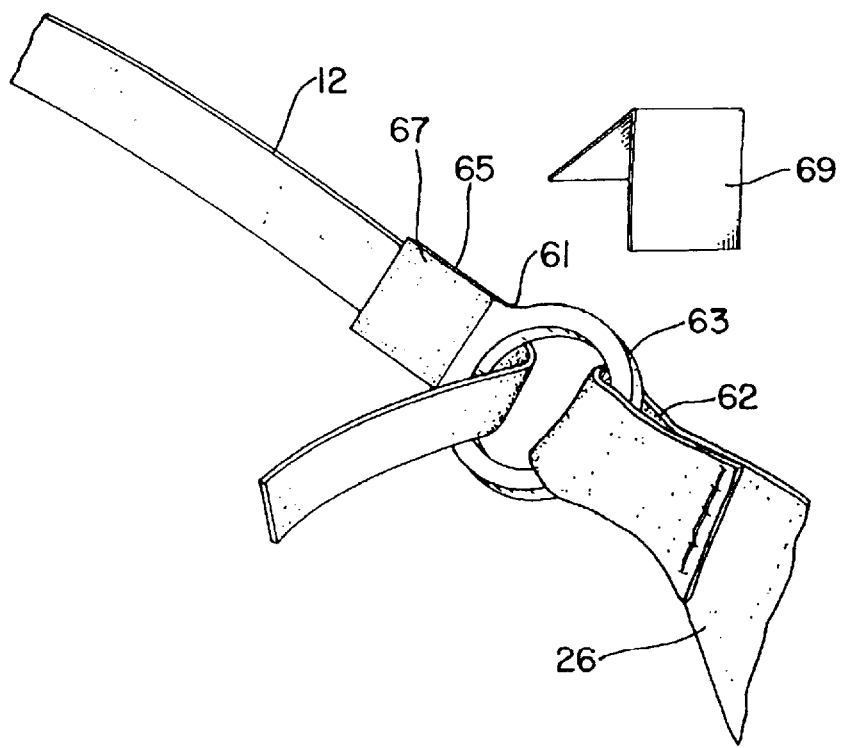
FIG. 7 is a perspective view of yet another alternative fastening means for the male genitalia supporter of the present invention.

An alternative fastening means 61 is shown in FIG. 7, where the receptacle 26 has a loop 62. The fastener 61 has a ring 63 that is attached to the loop 62, and a tab 65. The tab 65 has an adhesive 67 encompassing the entire outer surface of the tab 65, including the front side and the back side. The waist strap 12 is placed through the ring 63, the waist strap 12 is adjusted through the ring 63 to provide the amount of support desired at the testicles, and then the waist strap 12 is folded back over upon itself and over the adhesive 67 so that the adhesive 67 fastens the waist strap 12 to the fastener 61. Prior to the supporter being in use, the fastener 61 is stored with an adhesive covering 69 over the adhesive 67 to maintain the adhesive tackiness.

Figure 8:
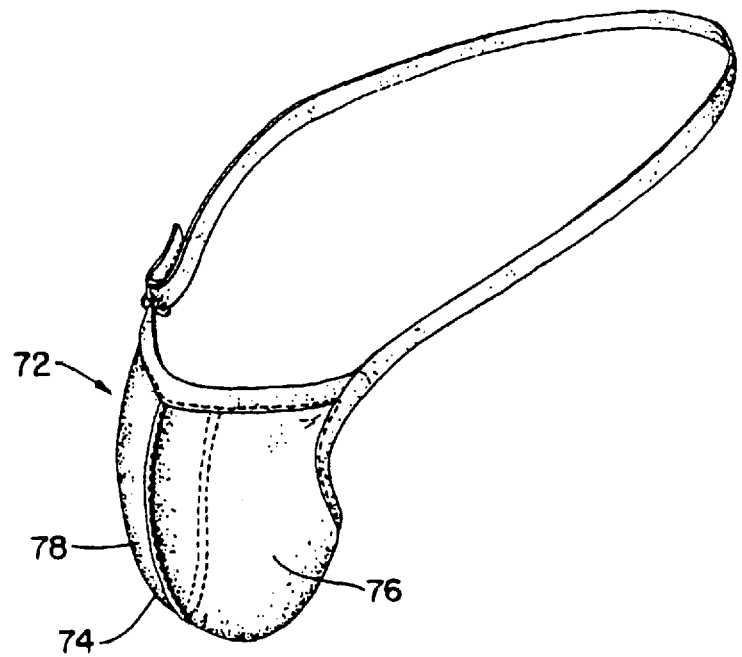
FIG. 8 is a perspective view of a separate embodiment of the present invention, wherein a receptacle has an opening for the penis.

As shown in FIG. 8, a separate embodiment of the present invention is disclosed, which is similar to the above embodiment except that a male genitalia support 72 has a receptacle 74 that has two overlapping flaps 76 and 78. The flaps 76 and 78 may be pulled apart easily by the wearer so that the support 72 has an opening for the wearer's penis to facilitate urination. This embodiment of the male genitalia support 72 would provide a continuous, non-variable amount of support for the wearer's testicular muscles and cords, even while the wearer performs necessary bodily functions.

Figure 9:
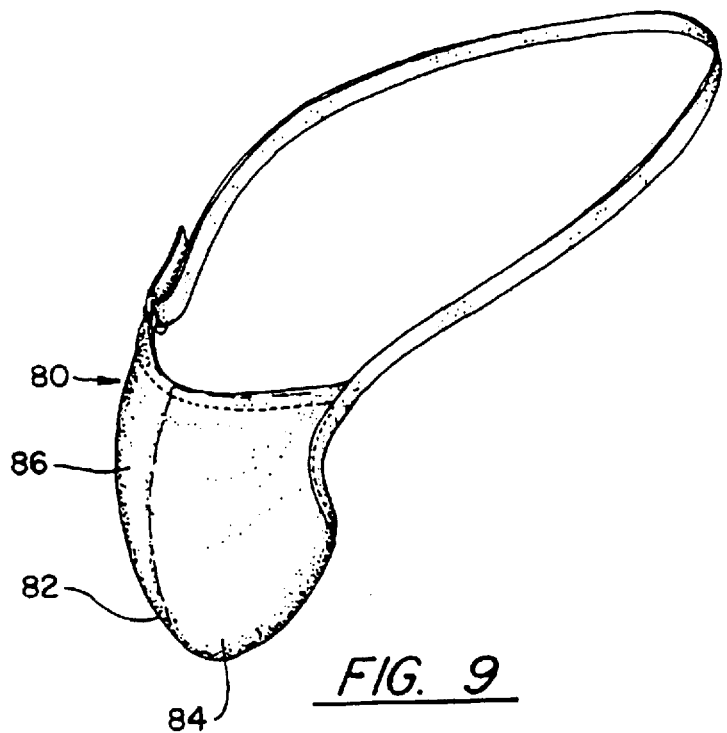
FIG. 9 is a perspective view of yet another embodiment of the present invention, wherein a receptacle has two compartments with one compartment being larger than the other.

As shown in FIG. 9, a separate embodiment of the present invention is disclosed. A male genitalia support 80 has a receptacle 82 that has a left compartment 84 and a right compartment 86. The left compartment 84 is shown to be slightly larger in relation to the right compartment 86 to accommodate for the predominately naturally occurring lower hanging left testicle of the wearer. Of course, the receptacle may have a larger right compartment in relation to the left compartment, or the compartments 84 and 86 may be equal, depending on the wearer's anatomical requirements.

Figure 10:
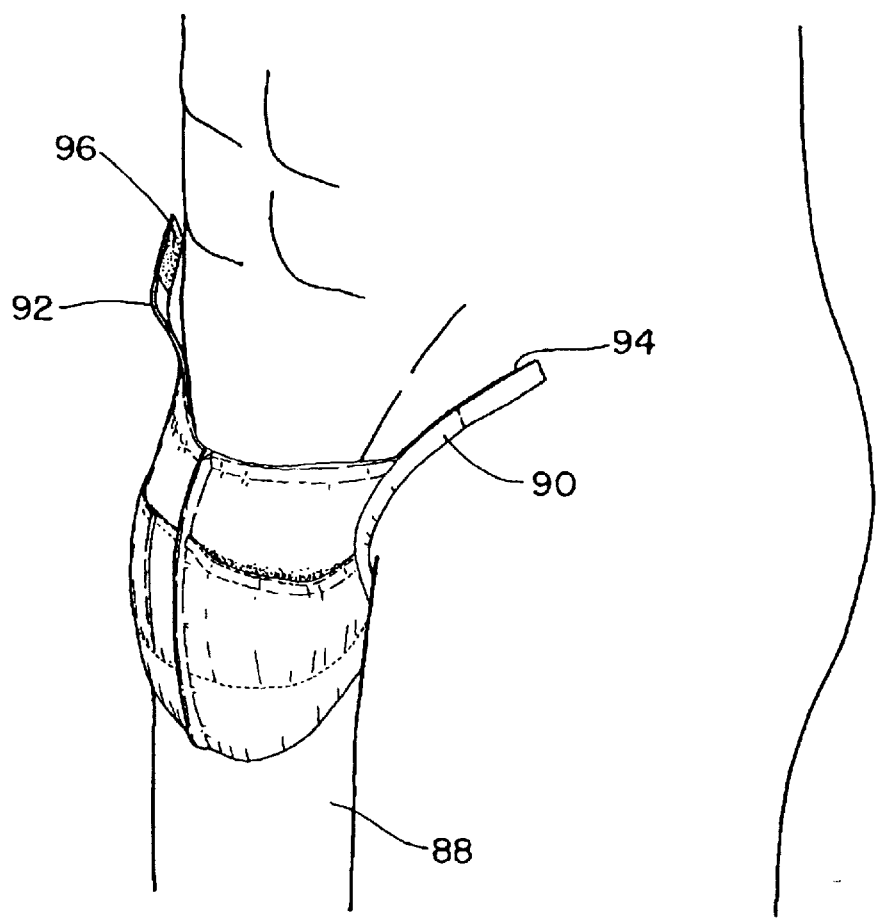
FIG. 10 is a perspective view of yet another embodiment of a supporter of the present invention, wherein a left waist band portion and a right waist band portion each have adhesive strips to attach the supporter to the wearer.

Now referring to FIG. 10, an alternative supporter 88 is shown, which is similar to the above alternative embodiment shown in FIG. 4, except that the supporter 88 has a left waist band portion 90 and a right waist band portion 92. Extending from and connected to the left waist band portion 90 is a right adhesive strip 94. Likewise, extending from and connected to the right waist band portion 92 is a right adhesive strip 96. This embodiment provides a supporter that does not require a waist band to encompass the torso of the wearer. Therefore, if a patient is bedridden, obese, or otherwise incapacitated, the placement of a waist band around the waist of the wearer is not required. The supporter 88 is placed into position, with the desired amount of support to the genitalia, then the adhesive strips are placed onto the skin of the wearer at the lower abdomen/hip region.

The absorbent male genitalia support of the present invention provides generally a constant and non-variable line of support to the testicular muscles and cords, relieving the testicular muscles and cords from excessive strain and tensile stress when the wearer requires extra support, such as after surgery, injury, or an illness. The male genitalia support of the present invention also provides an absorbent feature for absorbing discharge from the genitalia.

Now referring to FIG. 11, yet another alternative supporter 98 is shown, which is similar to the above alternative embodiment shown in FIG. 1, except that the supporter 98 is integrated with a garment, which may be a pair of boxer shorts, a swimsuit, or active wear; however, any garment with a waist portion and a genital covering portion would suffice.

Figure 13:
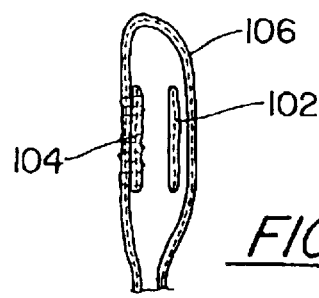
FIG. 13 is a close up view of the undergarment waistband shown in FIG. 12.

The supporter 98 has a posterior testicular strap 100 connected to a waist band portion 102. The waist band portion 102 is loosely housed in a garment waist band 106, so that the waist band 102 is free to move within the garment waist band and is independently adjustable without affecting the waist band of the garment. The waist band portion 102 at one side has an elastic portion 104 extending within the waist band portion 102. As shown in FIG. 13, the elastic portion 104 is secured internally of the garment waist band 106 with stitching. The garment waist band 106 has a first opening 108 to allow the elastic portion 104 to exit the garment waist band 106 when the garment is being put on. The waist band portion 102 is secured or stitched to the elastic portion 104 so that the elastic portion 104 keeps the waist band portion 102 secured to the garment waist band 106, while allowing the waist band portion 102 to stretch as needed when the garment is being placed over the buttocks of the wearer.

Figure 12:
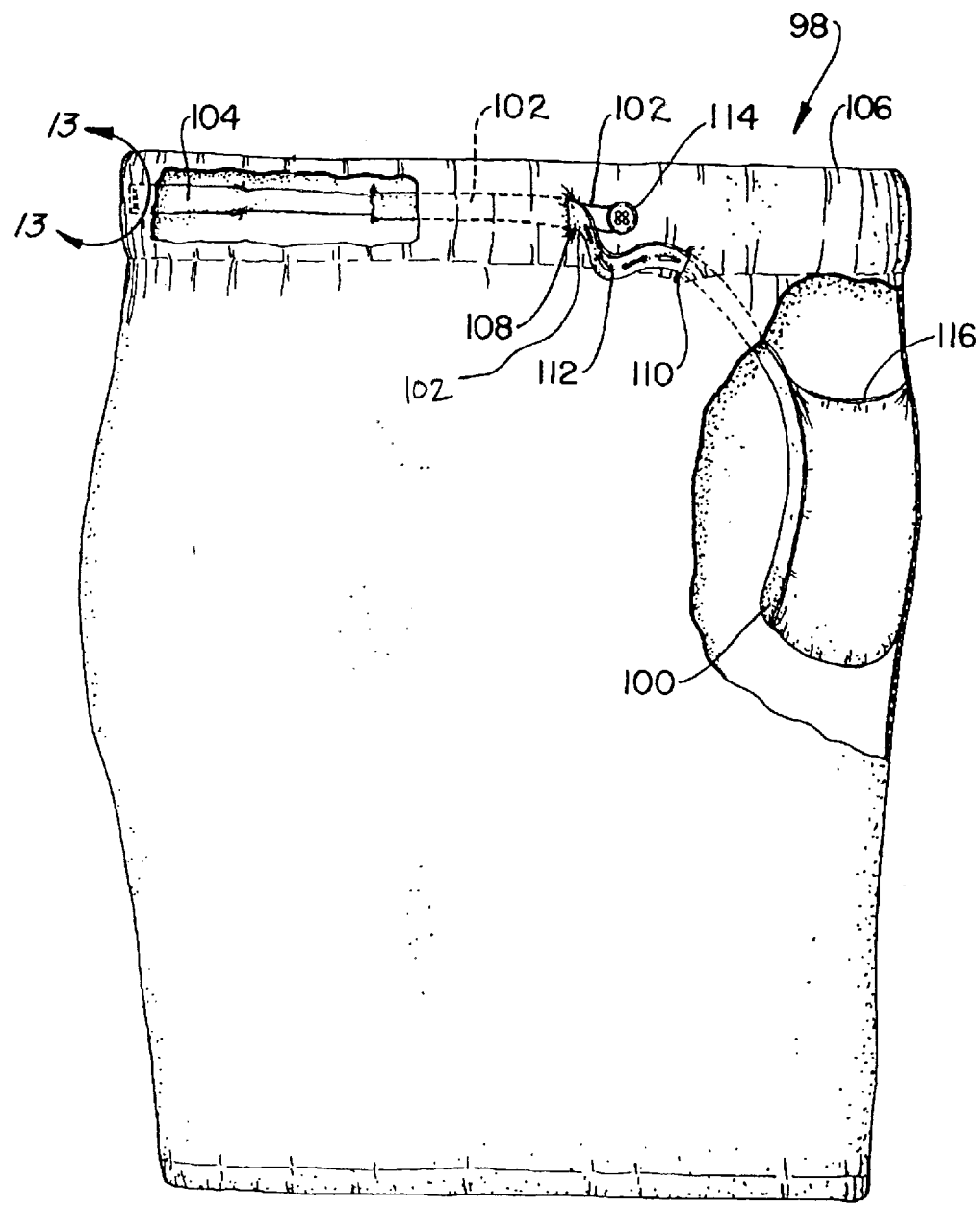
FIG. 12 is a cross sectional view showing the alternative embodiment male genitalia supporter incorporated into a garment.

As shown in FIG. 12, the garment waist band 106 further has a second opening 110 so that the waist band portion 102 can re-enter the garment waist band 106 and extend to the posterior testicular strap 100. The garment waist band 106 further has a third opening 111 that is opposite to the second opening 110 to facilitate the waist band portion 102 extending from the posterior testicular strap 100 at the opposite side.

An external button 114 is secured to the external side of the garment waist band 106. The waist band portion 102 has a plurality of complimentary button holes 112 so that when the garment is placed on the wearer and the posterior testicular strap 100 is adjusted to provide the desired amount of support, the waist band portion 102 is fastened or anchored into position by placing the button 114 through the appropriate buttonhole 112. The supporter 98 has enough slack 116 as shown in FIG. 12 to allow freedom of adjustment of the posterior testicular strap 100 without interference from the attachment point of the supporter 98 to the garment itself. Therefore, when the garment is worn by the wearer, the posterior testicular strap 100 is placed behind the wearer's genitals, and the posterior testicular strap 100 is adjusted through the waist band 102 to adjust the amount of support the posterior testicular strap 100 provides to the scrotal contents and the testicular muscles and cords.

Although this invention has been shown and described with respect to a detailed embodiment, those skilled in the art will understand that various changes in form and detail may be made without departing from the spirit and scope of the claimed invention.

We claim:

1. A male genitalia supporter, comprising:
    a posterior testicular strap portion adapted to be positioned on the posterior side of substantially supporting the wearer's scrotum and testicles when worn;
    a waist band portion that is adapted to be positioned around the waist of the wearer, said posterior testicular strap portion extending from said waist band portion;
    said posterior testicular strap portion and said waist band portion being made from a generally non-elastic material so that said posterior testicular strap portion relieves stress from and provides support to the wearer's testicular muscles and cords.

2. The male genitalia supporter of claim 1, wherein said posterior testicular strap portion is made from a generally non-elastic material so that a constant and non-variable amount of support is given to the testicular muscles and cords.

3. The male genitalia supporter of claim 1, wherein said waist band portion has means for adjusting the length of said waist band portion to accommodate different waist sizes and to adjust the amount of support given by said posterior testicular strap portion.

4. The male genitalia supporter of claim 1, further comprising:
    a receptacle attached to said posterior testicular strap portion, said receptacle accepting and housing the wearer's scrotum and testicles.

5. The male genitalia supporter of claim 4, wherein said receptacle is made of an air-permeable material so that ventilation is allowed through said receptacle.

6. The male genitalia supporter of claim 4, wherein said receptacle further comprises a means for thermal conditioning the wearer's genitalia.

7. The male genitalia supporter of claim 6, wherein said means for thermal conditioning further comprises at least one pocket attached to said receptacle.

8. The male genitalia supporter of claim 7, wherein said means for thermal conditioning further comprises a left pocket to thermally condition the left testicle and a right pocket to thermally condition the right testicle.

9. The male genitalia supporter of claim 8, wherein said pockets each further comprises a pleat, so that said supporter has a streamlined appearance until said thermal conditioning means is needed.

10. The male genitalia supporter of claim 4, wherein said receptacle houses a means for absorbing discharge from the genitalia.

11. The male genitalia supporter of claim 10, wherein said means for absorbing discharge from the genitalia comprises a layer of absorbent material adapted to be positioned adjacent to the genitalia.

12. The male genitalia supporter of claim 10, wherein said means for absorbing discharge from the genitalia further comprises at least one layer of cotton fiber adapted to be positioned adjacent to the genitalia.

13. The male genitalia supporter of claim 11, which further comprises a layer of non-stick material adjacent to said layer of absorbent material, so that said absorbent layer is sandwiched between the receptacle and said non-stick layer, said non-stick layer being adapted to be positioned adjacent to said wearer's genitalia.

14. The male genitalia supporter of claim 13, wherein said non-stick layer further comprises a layer of relatively thin plastic adapted to be positioned adjacent to said genitalia, said plastic having a plurality of relatively small openings so that discharge from the genitalia may be absorbed by said absorbent layer.

15. The male genitalia supporter of claim 4, further comprising:
a lateral strap portion extending laterally from said waist band portion and adapted to be positioned across the wearer's lower torso area.

16. The male genitalia supporter of claim 15, wherein said receptacle is attached to said posterior testicular strap portion and to said lateral strap portion.

17. The male genitalia supporter of claim 4, further comprising:
said receptacle having a left compartment and a right compartment, one of said compartments being larger than other said compartment to accommodate for anatomical differences in testicular size, length, and shape.

18. The male genitalia supporter of claim 4, wherein said receptacle further comprises two overlapping flaps adapted to be easily pulled apart by the wearer so that said supporter has an opening for the wearer's penis to facilitate bodily functions.

19. The male genitalia supporter of claim 4, wherein the receptical further has a perforation to allow a section of the recepticle to be removed so that the recepticle houses the wearer's scrotum and testicles only.

20. The male genitalia supporter of claim 1, further comprising a means for absorbing discharge from the genitalia.

21. The male genitalia supporter of claim 1, wherein the supporter is sewn into an existing piece of clothing, wherein said waist strap and said posterior testicular strap are independently connected to said piece of clothing so that said posterior testicular strap and said waist strap may be independently adjusted from said piece of clothing.

22. The male genitalia supporter of claim 21, wherein said piece of clothing has a means for fastening to said posterior testicular strap or said waist strap.

23. The male genitalia supporter of claim 22, wherein said piece of clothing means for fastening includes an external button fastened to the undergarment or garment and a plurality of button holes on said supporter waist band.

24. The male genitalia supporter of claim 22, wherein said supporter waist band further comprises an elastic portion secured to said piece of clothing.

25. The male genitalia supporter of claim 22, further comprising:
a receptacle attached to said posterior testicular strap portion, said receptacle accepting and housing the wearer's scrotum and testicles.

26. A male genitalia supporter, comprising:
a posterior testicular strap portion and a waist band portion, said posterior testicular strap portion extending from said waist band portion, said posterior testicular strap portion and said waist band portion being made from a generally non-elastic or material, said waist band portion having means for fastening so that said male genitalia supporter may be fastened around the wearer's waist, so that when said posterior testicular substantially on the posterior side of the wearer's scrotum and testicles, and said waist band portion is positioned around the wearer's waist, said male genitalia supporter relieves the wearer's testicular muscles and cords from tensile stress.

27. The male genitalia supporter of claim 26, said waist band portion further comprising means for adjusting the length of said waist band portion, so that the amount of support given by said male genitalia supporter to the wearer's testicular muscles and cords may be adjusted.

28. The male genitalia supporter of claim 26, wherein said posterior testicular strap portion and said waist band portion are made from a generally non-elastic material so that a constant and non-variable amount of support is given to the wearer's testicular muscles and cords.

29. The male genitalia supporter of claim 26, said supporter further comprises a line of support given by said posterior testicular strap portion to the wearer's testicular muscles and cords.

30. The male genitalia supporter of claim 29, said line of support further comprising:
a horizontal force vector and a vertical force vector, said force vectors combining to result in a resultant force vector defining said line of support.

31. The male genitalia supporter of claim 26, further comprising:
a receptacle attached to said posterior testicular strap portion, said receptacle housing the wearer's scrotum and testicles.

32. The male genitalia supporter of claim 31, wherein said receptacle is made of an air-permeable material so that ventilation is allowed through said receptacle.

33. The male genitalia supporter of claim 32, wherein said receptacle further comprises a means for thermal conditioning the wearer's genitalia.

34. The male genitalia supporter of claim 33, wherein said means for thermal conditioning further comprises at least one pocket attached to said receptacle.

35. The male genitalia supporter of claim 34, wherein said pocket further comprises a pleat, so that said supporter has a streamlined appearance until said thermal conditioning means is needed.

36. The absorbent male genitalia supporter of claim 31, further comprising:
a lateral strap portion extending laterally from said waist band portion across the wearer's lower torso area.

37. The absorbent male genitalia supporter of claim 36, wherein said receptacle is attached to said posterior testicular strap portion and to said lateral strap portion.

38. The absorbent male genitalia supporter of claim 31, further comprising:
said receptacle having a left compartment and a right compartment, one of said compartments being larger than said other compartment to accommodate for anatomical differences in testicular size, length, and shape.

39. The male genitalia supporter of claim 31, wherein said supporter is sewn into an existing piece of clothing.

40. The male genitalia supporter of claim 31, wherein said receptacle further comprises two overlapping flaps that may be pulled apart by the wearer so that said supporter has an opening for the wearer's penis to facilitate bodily functions.

41. The male genitalia supporter of claim 26, further comprising a means for absorbing discharge from the genitalia.

42. The male genitalia supporter of claim 26, wherein said waist band portion fastening means is an adhesive strip of material extending from said waist band portion.

43. The male genitalia supporter of claim 26, wherein said waist band portion further comprises a right waist band portion and a left waist band portion, said right waist band portion and said left waist band portion extending from said receptacle, a right adhesive strip extending from said right waist band portion and a left adhesive strip extending from said left waist band portion.

* * * * *